United States Patent
Chen et al.

(10) Patent No.: US 6,852,131 B1
(45) Date of Patent: Feb. 8, 2005

(54) ARTIFICIAL KNEE JOINT WITH A PUSH ROD BIASED TO ROTATE A PROSTHETIC LOWER LEG RAPIDLY TO ALIGN WITH A RESIDUAL THIGH

(76) Inventors: Chien-Liang Chen, 7F, No. 136, Sec. 2, Ho-Ping W. Rd., Taipei City (TW); Chien-Chuan Chen, 7F, No. 136, Sec. 2, Ho-Ping W. Rd., Taipei City (TW); I-Chun Chen, 7F, No. 136, Sec. 2, Ho-Ping W. Rd., Taipei City (TW)

( * ) Notice: Subject to any disclaimer, the term of this patent is extended or adjusted under 35 U.S.C. 154(b) by 0 days.

(21) Appl. No.: 10/642,220

(22) Filed: Aug. 18, 2003

(51) Int. Cl.[7] ............................... A61F 2/64; A61F 2/68
(52) U.S. Cl. ...................................................... 623/46
(58) Field of Search ................................. 623/39–46

(56) References Cited

U.S. PATENT DOCUMENTS

| | | | | |
|---|---|---|---|---|
| 4,005,496 A | * | 2/1977 | Wilkes | 623/44 |
| 4,145,766 A | * | 3/1979 | May | 623/45 |
| 5,728,173 A | * | 3/1998 | Chen | 623/44 |
| 5,755,813 A | * | 5/1998 | Krukenberg | 623/44 |
| 5,904,721 A | * | 5/1999 | Henry et al. | 623/26 |
| 6,517,585 B1 | * | 2/2003 | Zahedi et al. | 623/24 |
| 6,706,074 B1 | * | 3/2004 | Chen | 623/44 |

* cited by examiner

Primary Examiner—Bruce E Snow
(74) Attorney, Agent, or Firm—Foley & Lardner LLP

(57) ABSTRACT

An artificial knee joint includes a joint seat, a support frame, a hydraulic device, a push rod, and a biasing member. The joint seat has a joint body and a rotatable member connected pivotally to the joint body and connected fixedly to a residual thigh. The support frame is connected rotatably to the joint body, and is connected fixedly to a prosthetic lower leg. The push rod is movable relative to the joint body between an extended position, where a free end of the rotatable member is spaced apart from the joint body to align the lower leg with the thigh, and a retracted position, where the free end of the rotatable member abuts against the joint body. The biasing member biases the push rod to the extended position.

5 Claims, 5 Drawing Sheets

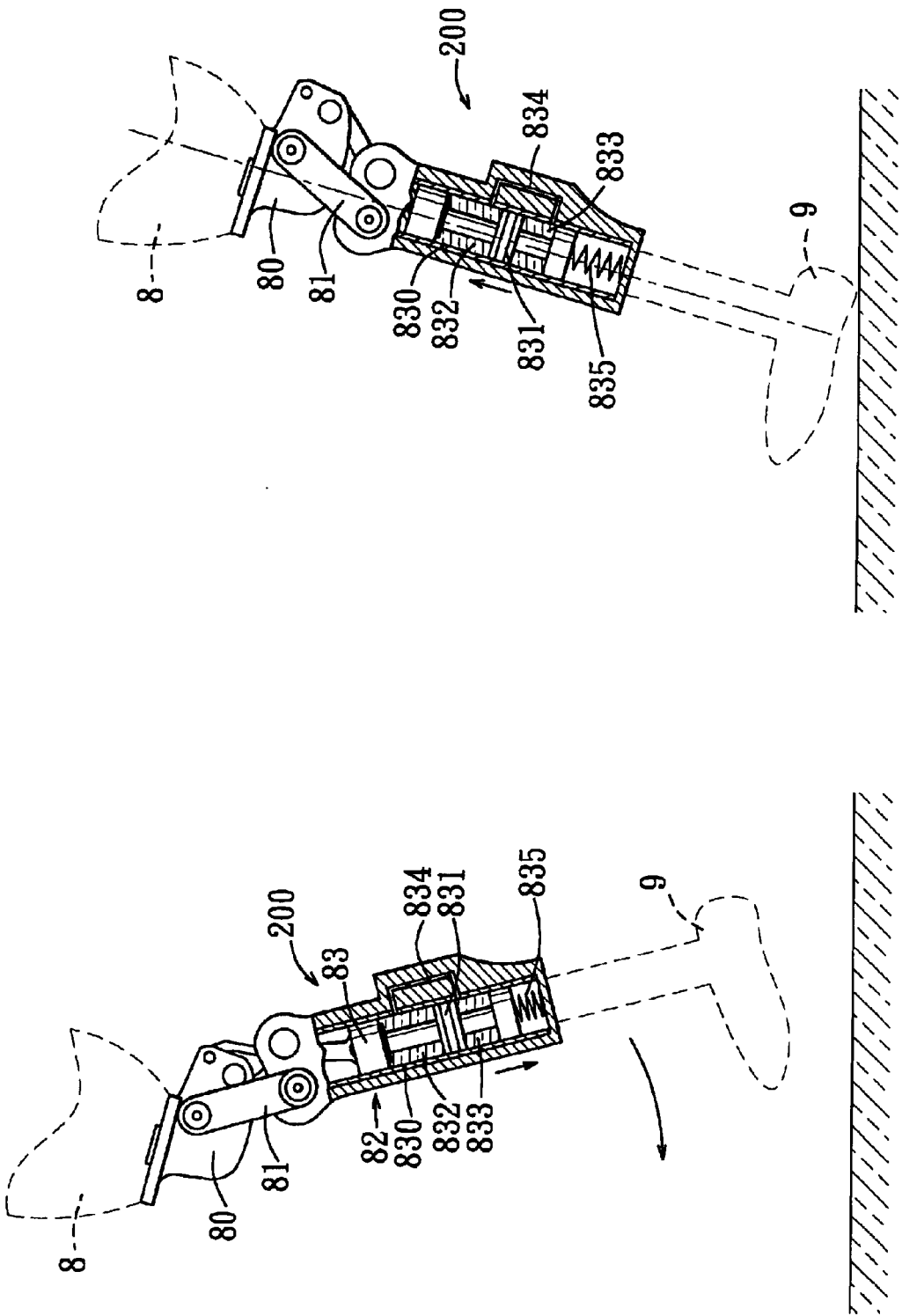

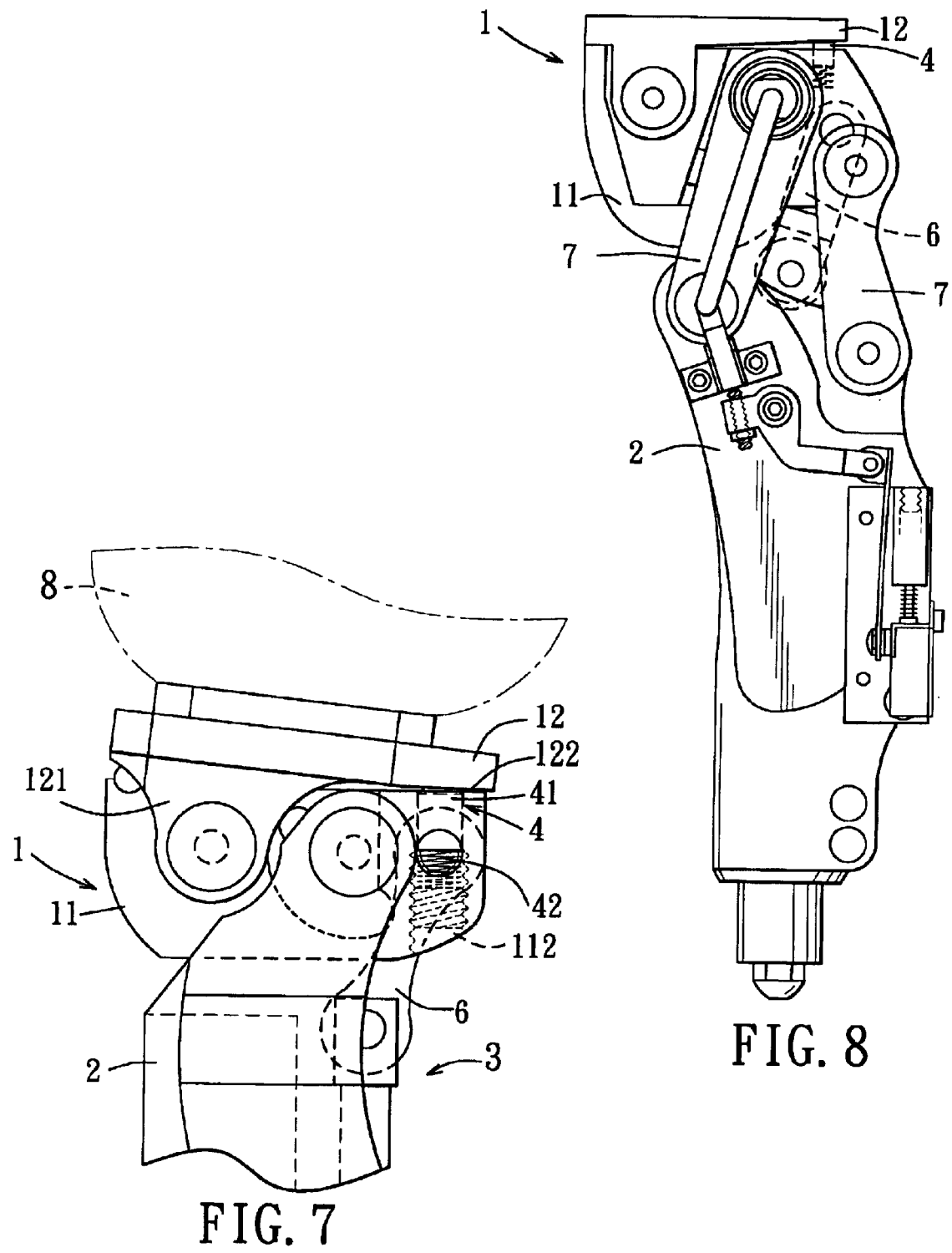

ARTIFICIAL KNEE JOINT WITH A PUSH ROD BIASED TO ROTATE A PROSTHETIC LOWER LEG RAPIDLY TO ALIGN WITH A RESIDUAL THIGH

BACKGROUND OF THE INVENTION

1. Field of the Invention

This invention relates to an artificial knee joint, and more particularly to an artificial knee joint that includes a push rod biased to rotate a prosthetic lower leg rapidly to align with a residual thigh.

2. Description of the Related Art

Referring to FIGS. 1 and 2, a conventional artificial knee joint 200 is shown to include a joint seat 80, two links 81 (only one is shown), a support frame 82, and a hydraulic device 83. The joint seat 80 is connected fixedly to a thigh 8 of the prosthesis wearer, and is connected rotatably to the support frame 82 by the links 81. The hydraulic device 83 includes a cylinder body 830 that has upper and lower oil chambers 832, 833, and a piston rod 831 that is connected to the links 81 and that is movable within the cylinder body 830. The upper and lower oil chambers 832, 833 are in fluid communication with each other via an oil passage 834. As such, the hydraulic device 83 can retard relative rotation of the thigh 8 and the lower leg 9 during extension and flexion of the artificial knee joint 200.

When the thigh 8 is raised to flex the joint 200, as shown in FIG. 1, a coiled compression spring 835 is compressed by the piston rod 831. Subsequently, when the thigh 8 is turned frontwardly to align the thigh 8 with the lower leg 9, as shown in FIG. 2, the coiled compression spring 835 returns to its stretched state. Although the coiled compression spring 835 can push the piston rod 831 upwardly so as to bias the thigh 8 to align with the lower leg 9 during movement of the artificial knee joint 200 from the flexed position shown in FIG. 1 to the extended position shown in FIG. 2, the movement of the piston rod 831 is retarded due to presence of hydraulic liquid within the cylinder body 830 so that it takes a relatively long time to rotate the lower leg 9 relative to the thigh 8 from the position shown in FIG. 1 to that shown in FIG. 2. As such, the lower leg 9 may not be able to align with the thigh 8 when the lower leg 9 is pressed against the ground by the thigh 8 during fast walking, thereby resulting in falling of the prosthesis wearer.

SUMMARY OF THE INVENTION

The object of this invention is to provide an artificial knee joint that includes a push rod biased to rotate a prosthetic lower leg rapidly to align with a residual thigh.

According to this invention, an artificial knee joint includes a joint seat, a support frame, a hydraulic device, a push rod, and a biasing member. The joint seat has a joint body and a rotatable member connected pivotally to the joint body and connected fixedly to a residual thigh of a prosthesis wearer. The support frame is connected rotatably to the joint body, and is connected fixedly to a prosthetic lower leg. The push rod is disposed movably within the joint body, and is movable between an extended position, where the push rod projects from the joint body and where a free end of the rotatable member is spaced apart from the joint body to align the lower leg with the thigh, and a retracted position, where the push rod is retracted into the joint body and where the free end of the rotatable member abuts against the joint body. The biasing member biases the push rod to the extended position so that the free end of the rotatable member turns away from the joint body.

BRIEF DESCRIPTION OF THE DRAWINGS

These and other features and advantages of this invention will become apparent in the following detailed description of the preferred embodiments of this invention, with reference to the accompanying drawings, in which:

FIG. 1 is a partly sectional, schematic side view of a conventional artificial knee joint, which is in a flexed state;

FIG. 2 is a partly sectional, schematic side view of the conventional artificial knee joint, which is in an extended state;

FIG. 7 is a side view of the first preferred embodiment, illustrating a retracted position of a push rod of one pushing unit of the pushing device; and FIG. 8 is a side view of the second preferred embodiment of an artificial knee joint according to this invention.

DETAILED DESCRIPTION OF THE PREFERRED EMBODIMENTS

Figure 3:
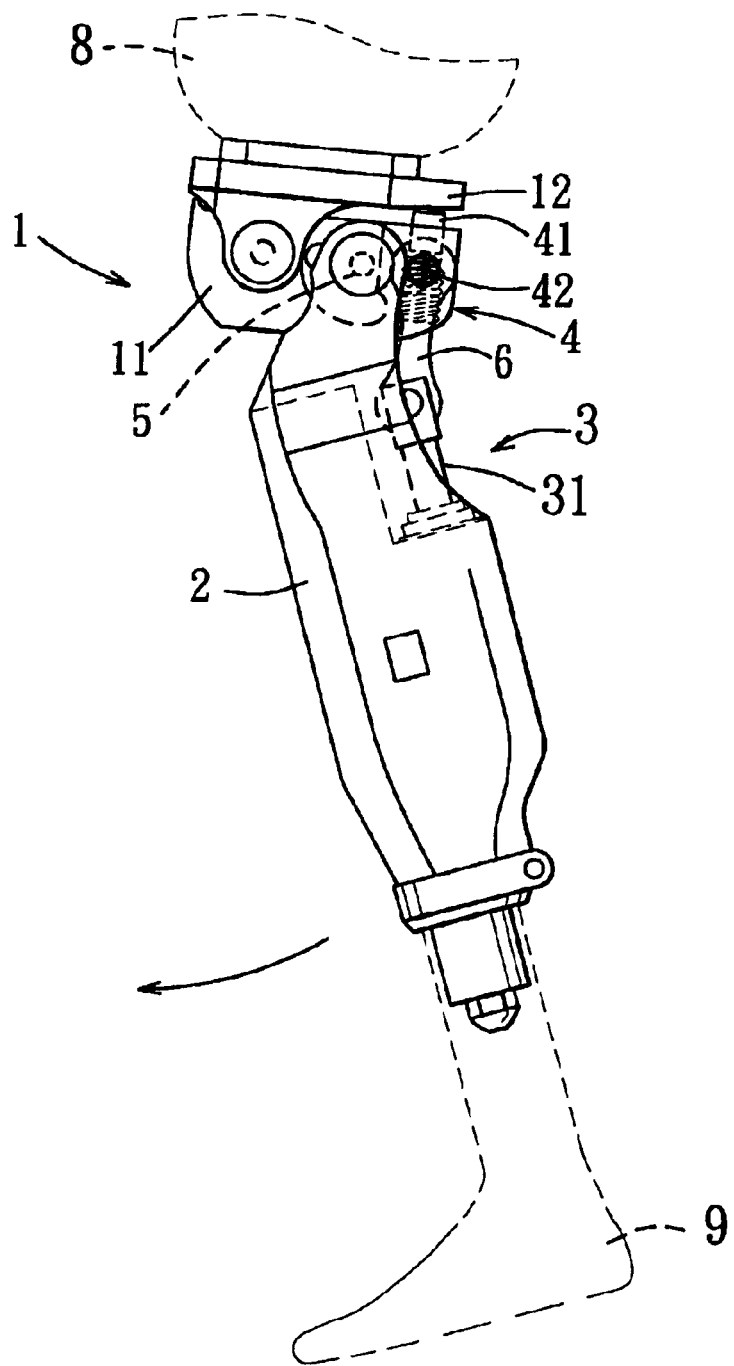
FIG. 3 is a schematic side view of the first preferred embodiment of an artificial knee joint according to this invention, which is in a flexed state.
Figure 4:
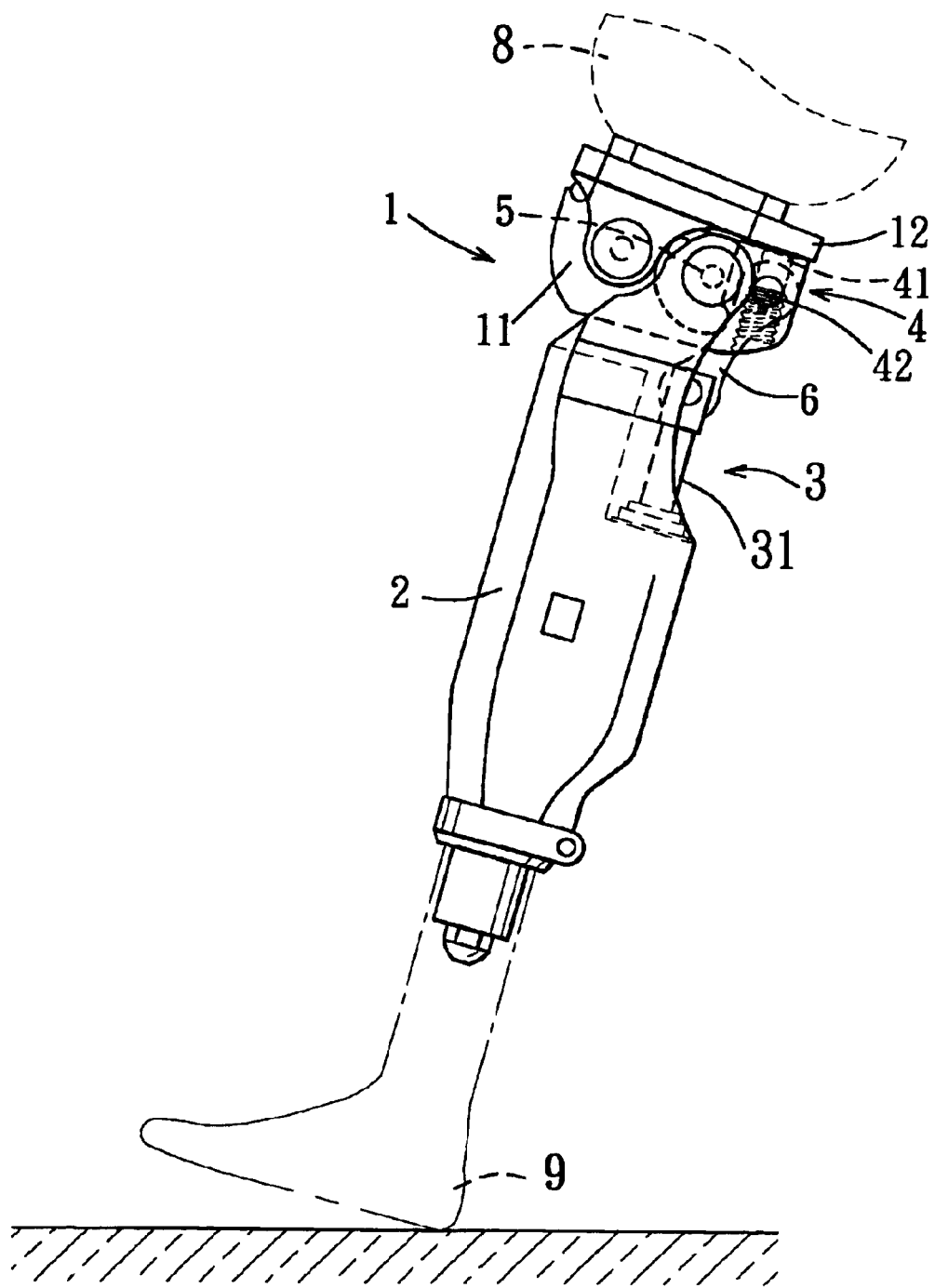
FIG. 4 is a side view of the first preferred embodiment, which is in an extended state.

Before the present invention is described in greater detail in connection with the preferred embodiments, it should be noted that similar elements and structures are designated by like reference numerals throughout the entire disclosure.

Referring to FIGS. 3, 4, 5, and 6, the first preferred embodiment of an artificial knee joint according to this invention is shown to include a joint seat 1, a hollow support frame 2, a hydraulic device 3, and a pushing device 4 consisting of two pushing units 40 (see FIG. 6), each of which includes a push rod 41, a biasing member 42, and an adjustment bolt 43.

Figure 6:
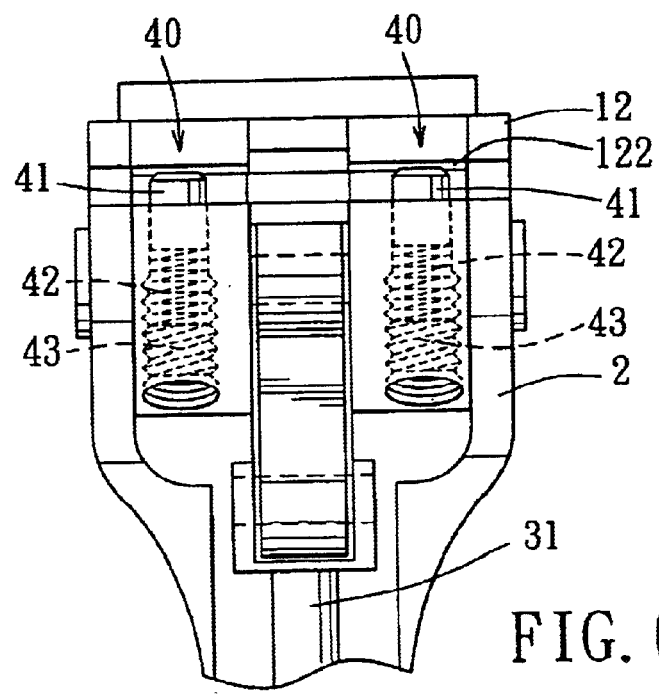
FIG. 6 is a schematic rear view of the first preferred embodiment, illustrating the positions of two pushing units of the pushing device relative to a piston rod.

The joint seat 1 includes a joint body 11 and a rotatable member 12 that is adapted to be connected fixedly to a residual thigh 8 of a prosthesis wearer and that has a pivot end 121 connected pivotally to the joint body 11, and a free end 122. The rotatable member 12 is configured generally as a horizontal plate. The support frame 2 has a lower end that is adapted to be connected fixedly to a prosthetic lower leg 9. A connecting unit includes a horizontal pivot pin 5 extending into an upper end of the support frame 2 and the joint body 11 so as to connect the upper end of the support frame 2 rotatably to the joint body 11 to thereby permit rotation of the lower leg 9 relative to the thigh 8. The hydraulic device 3 is disposed within the support frame 2, and has a piston rod 31 that is disposed movably in the support frame 2 and that is connected pivotally to a link 6, which is connected pivotally to the joint body 11. The pushing units 40 are located at two sides of the piston rod 31, as shown in FIG. 6. Since the pushing units 40 are identical in construction, only one of the pushing units 40 will be described in the succeeding paragraph.

Figure 5:
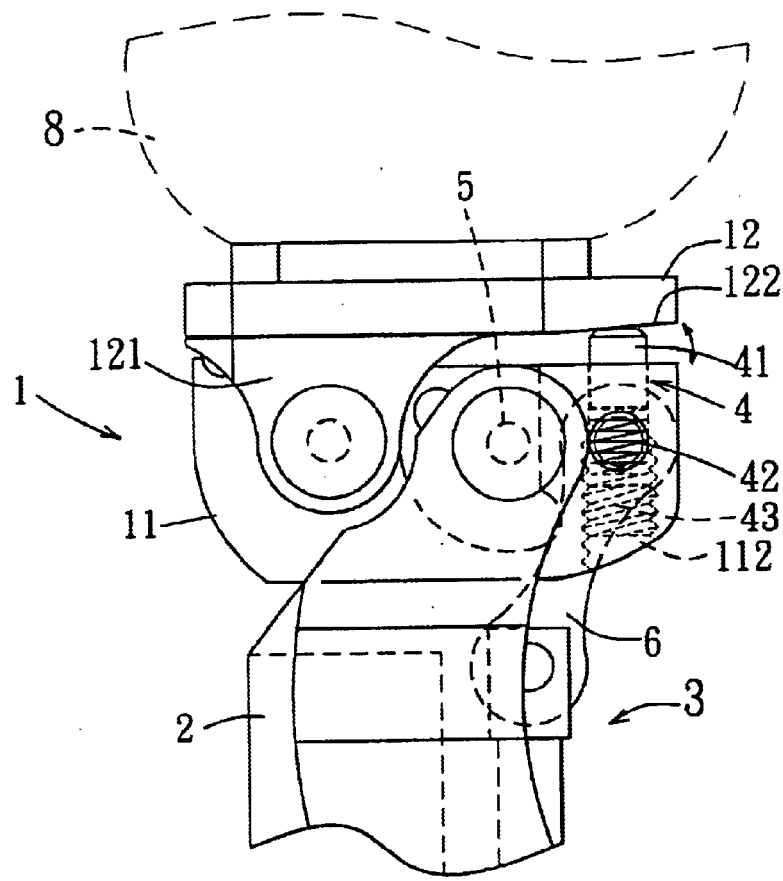
FIG. 5 is a side view of the first preferred embodiment, illustrating arrangement of a pushing device.

The push rod 41 is disposed movably within a vertical hole 112 in a top surface of the joint body 11, and is movable between an extended position shown in FIG. 5, where an upper end of the push rod 41 projects from the joint body 11 and where the free end 122 of the rotatable member 12 is spaced apart from a rear end of the joint body 11 to permit the lower leg 9 to align with the thigh 8, and a retracted position shown in FIG. 7, where the upper end of the push rod 41 is retracted into the joint body 11 and where the free end 122 of the rotatable member 12 abuts against the rear end of the joint body 11. The biasing member 42 is configured as a coiled compression spring, and is disposed within the vertical hole 112 in the joint body 11 so as to press the push rod 41 upward against the free end 122 of the rotatable member 12. As such, when no external force is applied to the free end 122 of the rotatable member 12, the push rod 41 is biased by the biasing member 42 to its extended position, thereby facilitating movement of the lower leg 9 to a full extension position, where the lower leg 9 is aligned with the thigh 8. The adjustment bolt 43 is disposed in the vertical hole 112 in the joint body 11 and immediately under the biasing member 42, and is adjustable to change the biasing force of the biasing member 42.

When the artificial knee joint is flexed to deflect the lower leg 9 from the thigh 8, the free end 122 of the rotatable member 12 turns downward relative to the joint body 11 such that the push rod 41 is pressed by the free end 122 of the rotatable member 12 to move from the extended position shown in FIG. 5 to the retracted position shown in FIG. 7. At this time, the biasing member 42 is compressed, and is able to provide a restoration force for returning the push rod 41 to the extended position so as to rotate the lower leg 9 rapidly to align with the thigh 8 when the rotatable member 12 is released.

FIG. 8 shows the second preferred embodiment of an artificial knee joint according to this invention, which is similar to the previous preferred embodiment in construction. Unlike the previous preferred embodiment, the connecting unit includes four upright links 7 (only two are shown), each of which has an upper end that is connected pivotally to the joint body 11 in a known manner, and a lower end that is connected pivotally to the upper end of the support frame 2 in a known manner.

With this invention thus explained, it is apparent that numerous modifications and variations can be made without departing from the scope and spirit of this invention. It is therefore intended that this invention be limited only as indicated by the appended claims.

We claim:

1. An artificial knee joint for connecting a residual thigh of a prosthetic wearer to a prosthetic lower leg, said knee joint comprising:

a joint seat including a joint body and a rotatable member that is adapted to be connected fixedly to the thigh and that has a pivot end connected pivotally to said joint body, and a free end;

a hollow support frame having an upper end and a lower end that is adapted to be connected fixedly to the lower leg;

a connecting unit for connecting said upper end of said support frame rotatably to said joint body so as to permit rotation of the lower leg relative to the thigh;

a hydraulic device disposed within said support frame and having a piston rod that is disposed movably in said support frame and that is connected to said joint body;

a push rod disposed movably within said joint body and movable between an extended position, where an upper end of said push rod projects from said joint body and where said free end of said rotatable member is spaced apart from said joint body to align the lower leg with the thigh, and a retracted position, where said upper end of said push rod is retracted into said joint body and where said free end of said rotatable member abuts against said joint body; and a biasing member for biasing said push rod to said extended position so that said free end of said rotatable member turns away from said joint body, thereby facilitating movement of the lower leg to a full extension position, where the lower leg is aligned with the thigh.

2. The artificial knee joint as claimed in claim 1, wherein said rotatable member is configured generally as a horizontal plate, said joint body having a top surface that is formed with a vertical hole, said push rod being disposed within said vertical hole in said joint body, said biasing member being configured as a coiled compression spring and being disposed within said vertical hole in said joint body so as to press said push rod upward against said free end of said rotatable member.

3. The artificial knee joint as claimed in claim 2, wherein said joint body further has an adjustment bolt that is disposed in said vertical hole and immediately under said coiled compression spring and that is adjustable to change biasing force of said coiled compression spring.

4. The artificial knee joint as claimed in claim 1, wherein said connecting unit includes a horizontal pivot pin extending into said upper end of said support frame and said joint body.

5. The artificial knee joint as claimed in claim 1, wherein said connecting unit includes four upright links, each of which has an upper end that is connected pivotally to said joint body, and a lower end that is connected pivotally to said upper end of said support frame.

* * * * *